(12) United States Patent
Ishikawa et al.

(10) Patent No.: US 8,265,734 B2
(45) Date of Patent: Sep. 11, 2012

(54) IMAGING AND DISPLAYING SYSTEM WITH IMAGING UNIT AND DISPLAY UNIT WHICH ARE SUPPORTED BY MOVABLE ARM

(75) Inventors: Tomonori Ishikawa, Tokyo (JP); Junichi Nozawa, Sagamihara (JP); Motokazu Nakamura, Tokyo (JP); Satoshi Otsuka, Tokyo (JP)

(73) Assignee: Olympus Corporation (JP)

( * ) Notice: Subject to any disclaimer, the term of this patent is extended or adjusted under 35 U.S.C. 154(b) by 1486 days.

(21) Appl. No.: 11/095,389

(22) Filed: Mar. 31, 2005

(65) Prior Publication Data
US 2005/0228257 A1 Oct. 13, 2005

(30) Foreign Application Priority Data

Mar. 31, 2004 (JP) ................................ 2004-104957

(51) Int. Cl.
*A61B 6/00* (2006.01)
(52) U.S. Cl. ..................... 600/476; 600/407; 359/384
(58) Field of Classification Search .......... 600/101–102, 600/160, 166, 407, 437, 459–480; 359/368, 359/382–388
See application file for complete search history.

(56) References Cited

U.S. PATENT DOCUMENTS

| | | | | |
|---|---|---|---|---|
| 4,614,410 A * | 9/1986 | Ikenaga et al. | ................. | 359/368 |
| 4,621,531 A * | 11/1986 | Nakamura et al. | ............... | 73/606 |
| 4,863,133 A * | 9/1989 | Bonnell | ................... | 248/280.11 |
| 5,095,887 A * | 3/1992 | Leon et al. | ..................... | 600/166 |
| 5,579,772 A * | 12/1996 | Kinukawa et al. | ............ | 600/476 |
| 5,995,282 A * | 11/1999 | Akiyama et al. | ............... | 359/384 |
| 5,999,837 A * | 12/1999 | Messner et al. | ................ | 600/407 |
| 6,106,456 A * | 8/2000 | Storz | ............................. | 600/102 |
| 6,398,721 B1 * | 6/2002 | Nakamura et al. | ............ | 600/102 |
| 6,434,416 B1 * | 8/2002 | Mizoguchi et al. | ........... | 600/427 |
| 6,447,451 B1 * | 9/2002 | Wing et al. | ..................... | 600/437 |
| 6,575,908 B2 * | 6/2003 | Barnes et al. | ................. | 600/443 |
| 7,122,032 B2 * | 10/2006 | Shinmura et al. | ............... | 606/34 |
| 7,258,668 B2 * | 8/2007 | Hirooka et al. | ............... | 600/437 |
| 7,507,199 B2 * | 3/2009 | Wang et al. | .................... | 600/102 |
| 7,695,481 B2 * | 4/2010 | Wang et al. | .................... | 606/130 |
| 2002/0151784 A1 * | 10/2002 | Mizoguchi et al. | ........... | 600/407 |
| 2003/0151809 A1 * | 8/2003 | Takahashi et al. | ............ | 359/462 |
| 2006/0018017 A1 * | 1/2006 | Takahashi | ..................... | 359/466 |

(Continued)

FOREIGN PATENT DOCUMENTS

EP 0 293 760 A2 5/1988

(Continued)

OTHER PUBLICATIONS

Search Report issued by the European Patent Office on Mar. 18, 2010 in connection with corresponding European patent application No. EP 05 00 7074.

*Primary Examiner* — Sanjay Cattungal
(74) *Attorney, Agent, or Firm* — Ostrolenk Faber LLP (57) ABSTRACT

An imaging and displaying system comprises an imaging unit for acquiring images of a treatment site of a subject, a display unit for displaying the images acquired by the imaging unit, and a unit-to-unit connecting device for detachably connecting the imaging unit and the display unit. The imaging unit and the display unit are spatially and movably supported. At least one of the imaging unit and the display unit is detachably attached to an arm with a unit-to-arm detachable device therebetween.

27 Claims, 7 Drawing Sheets

U.S. PATENT DOCUMENTS

2006/0135866 A1 * 6/2006 Namii et al. .................. 600/407

FOREIGN PATENT DOCUMENTS

| JP | 56-20448 | 2/1981 |
| JP | 62-231208 | 10/1987 |
| JP | 63-296746 | 12/1988 |
| JP | 2001-51201 | 2/2001 |
| JP | 2001-276092 | 10/2001 |
| JP | 2002-6228 | 1/2002 |
| WO | WO 97/15144 | 4/1997 |
| WO | WO 99/58044 | 11/1999 |
| WO | WO 00/09001 | 2/2000 |
| WO | WO 01/45627 | 6/2001 |

* cited by examiner

IMAGING AND DISPLAYING SYSTEM WITH IMAGING UNIT AND DISPLAY UNIT WHICH ARE SUPPORTED BY MOVABLE ARM

CROSS REFERENCES TO RELATED APPLICATIONS

The present application relates to and incorporates by reference Japanese Patent application No. 2004-104957 filed on Mar. 31, 2004.

BACKGROUND OF THE INVENTION

1. Technical Field of the Invention

The present invention relates to a microscopic device comprising an imaging unit and a display unit, with which treatment can be given by observing enlarged images of a treatment site of a subject, by displaying images of the treatment site of a subject which have been picked up by the imaging unit, and in particularly, to a support system of the imaging unit and the display unit.

2. Related Art

In surgeries, such as in neurosurgery and otolaryngology, fine and precise operations are required to enhance performance of the surgeries. In order to facilitate such fine and precise operations, surgical microscopes, which can provide enlarged images of a treatment site of a subject, are typically used. In surgeries using such surgical microscopes, the site of a subject for treatment has to be treated from every direction. Therefore, a used microscope must be the one which is movable to and fixable at various positions and angles. To satisfy such demands, microscopes in general are supported by an arm having a plurality of movable parts. Devices involving such a type of support arm for microscopes are disclosed in Japanese patent published unexamined application No. 62-231208, Japanese patent published unexamined application No. 2001-276092, Japanese patent published unexamined application No. 63-296746 and Japanese patent published examined application No. 02-009820.

All of the surgical microscopes disclosed in the above references have an arrangement in which a body of a microscope for observing a treatment site of a subject is integrally provided. A body of such a microscope comprises an objective lens for taking flux of light from a treatment site of a subject and an ocular lens for an operator to peep therethrough enlarged optical images of the treatment site of a subject, and these lenses are integrated or assembled into an integrated housing to constitute an integrated structure. Therefore, in observing the treatment site of a subject in various conditions, the ocular lens naturally has to be moved simultaneously with the objective lens. Accordingly, every time the operator changes a portion of the site to be observed to another portion, the operator, per se, has to move. Further, when the body of the microscope is largely tilted to obliquely observe the treatment site of a subject, the operator is forced to carry out observation in a terrible posture. As a matter of course, a surgery is carried out while observing a treatment site of a subject, and therefore, such a terrible posture may sometimes result in hardly allowing the operator to carry out the surgery with ease, tending to cause the operator to suffer from fatigue.

In recent years, with the rapid advances in electronics, a trend of making electronic images is under way in the field of the surgical microscopes described above. Also, for the conventional optical microscopes, surgical microscopes of digital image system are now being attempted. Devices involving such a digital image system surgical microscope are disclosed in Japanese patent published unexamined application No. 2002-006228 and Japanese patent published unexamined application No. 2001-051201.

Unlike the surgical microscope described hereinbefore, the above mentioned references, i.e. Japanese patent published unexamined application No. 2002-006228 and Japanese patent published unexamined application No. 2001-051201, disclose an arrangement in which a part for taking flux of light (imaging unit) from a treatment site of a subject is provided separately from image display means (display unit). Thus, when the imaging unit is tilted for oblique observation of the treatment site, the display unit remains unmovable, which allows an operator to constantly maintain an easy posture. However, when an operator attempts to give treatment to a treatment site of a subject, the operator has to extend his/her arms in a direction deviated from his/her forward direction, i.e. in a direction that has little to do with a direction of his/her natural movement. Accordingly, the operator may again be forced to carry out a surgery in a posture suffering from his/her arms' fatigue and unnatural feeling.

Such unfavorable circumstances are advanced as the tilting or movement of an imaging unit becomes larger, causing more hindrance in carrying out a surgery under the microscopic observation. The problem of such hindrance may be removed if a display unit is moved to an optimum position every time an imaging unit is moved. However, it is apparent that such an operation is very troublesome.

SUMMARY OF THE INVENTION

The present invention has been made in light of the problems described above, and has as its object to provide an imaging and display system with which an imaging unit and a display unit may be supported in an optimum condition for use.

The imaging and display system of the present invention comprises an imaging unit for imaging a treatment site of a subject, a display unit for displaying images picked up by the imaging unit, and a unit-to-unit connecting device for detachably coupling the imaging unit and the display unit.

Preferably, this system may further comprise a first arm for supporting the imaging unit in a spatially movable manner, and a second arm for supporting the display unit in a spatially movable manner.

More preferably, at least one of the imaging unit and the display unit may be detachably attached to corresponding one of the first and the second arms via a unit-to-arm detachable device.

DETAILED DESCRIPTION OF THE PREFERRED EMBODIMENTS

First Embodiment

A monitor microscope (an image microscopic device) serving as an imaging and display system according to a first embodiment of the present invention is described below with reference to FIGS. 1 and 2.

As shown in these figures, this imaging microscopic device comprises an imaging unit 1 that serves as a means for picking up images of a treatment site of a subject, and a display unit 2 that serves as a means for displaying images picked up by the imaging unit 1. The imaging unit 1 and the display unit 2 are detachable from each other owing to a detachable coupling means, as will be described later.

Figure 1:
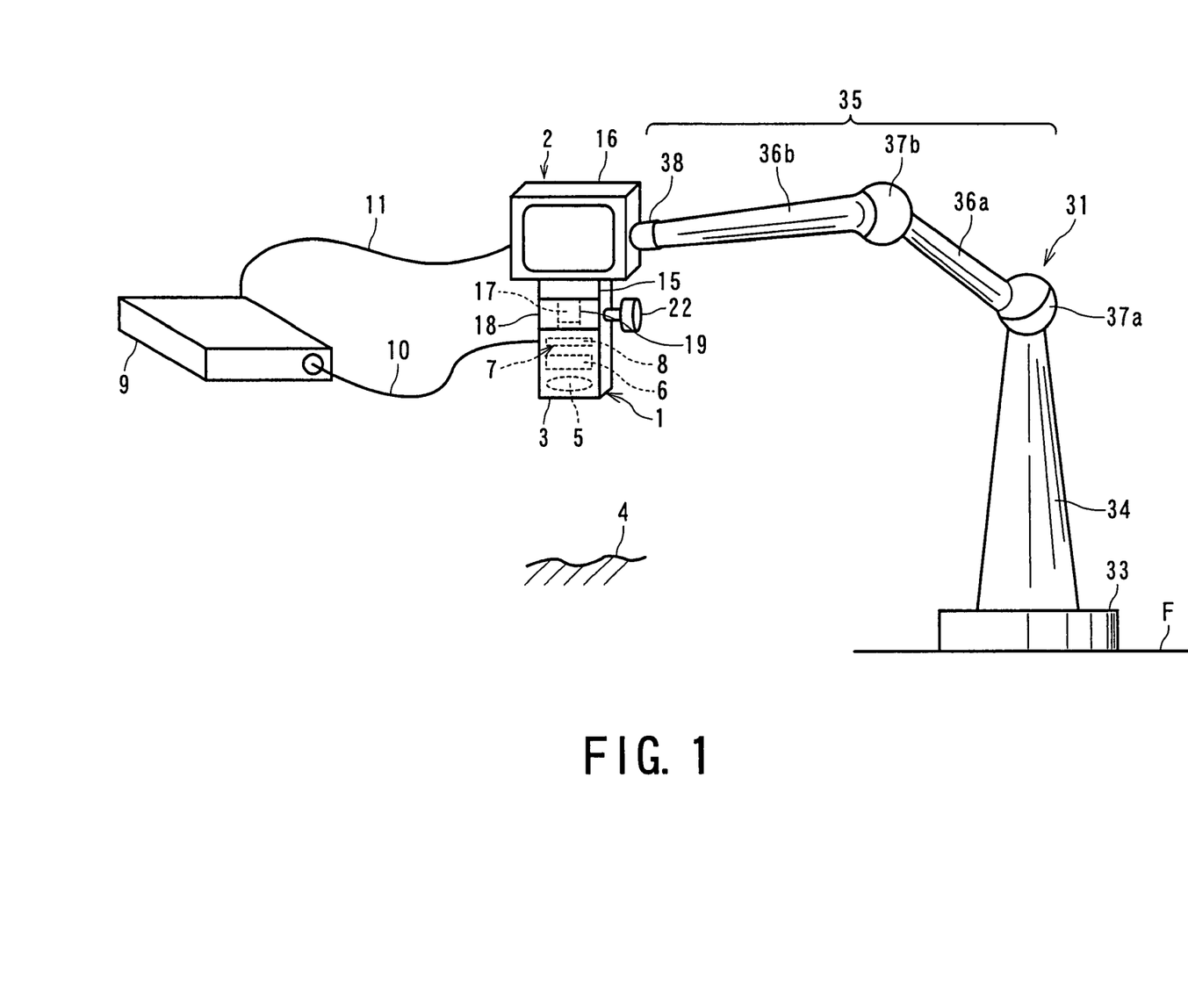
FIG. 1 is a schematic diagram of a monitor microscope in use, with an imaging unit and a display unit being coupled to each other, according to a first embodiment of the present invention.
Figure 2:
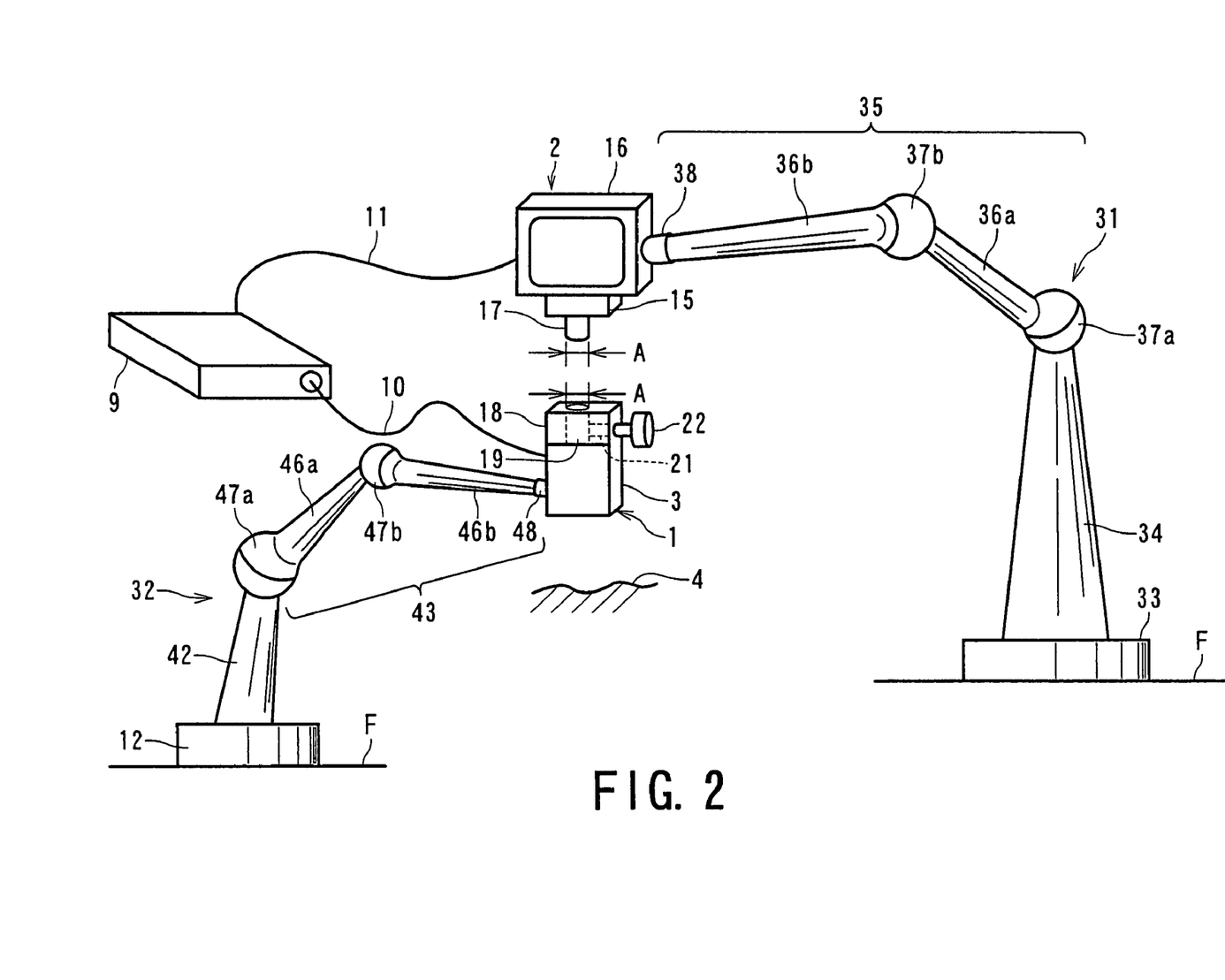
FIG. 2 is a schematic diagram of a monitor microscope in use, with an imaging unit and a display unit being separated from each other, according to the first embodiment of the present invention.

FIG. 1 shows a used state (first state of use) in which the imaging unit 1 and the display unit 2 are coupled to each other, and FIG. 2 shows another used state (second state of use) in which the imaging unit 1 and the display unit 2 are separated from each other.

The imaging unit 1 comprises a device housing 3 in which are disposed an objective lens 5 for taking flux of light from a treatment site 4 of a subject of a living organism, an imaging lens 6 on which the flux of light emitted from the objective lens 5 is incident, and an image pickup device 8 whose light receiving surface is positioned at a image forming position 7 of the imaging lens 6. A signal cable 10 for directing an image signal from the image pickup device 8 to a camera control unit (CCU) 9 is connected to the imaging unit 1. The CCU 9 is placed, being sufficiently apart from the imaging unit 1 and the display unit 2 so as not to stand in a way.

The display unit 2 is configured using an LCD, for example, with a video cable 11 from the CCU 9 mentioned above being connected thereto. This video cable 11 is adapted to direct a video signal from the CCU 9 to the display unit 2.

A first attaching/detaching part 15 for fixing the imaging unit 1 is provided at a lower surface of a device housing 16 of the display unit 2. As shown in FIG. 2, a fitting shaft 17 projecting downward and having a diameter A is provided at the first attaching/detaching part 15 so that the imaging unit 1 can be mounted on the display unit 2. Specifically, a second attaching/detaching part 18 for attachment of the display unit 2 is provided atop the device housing 3 of the imaging unit 1. In the second attaching/detaching part 18, a fitting hole 19 of the diameter A is formed to fit with the fitting shaft 17 of the display unit 2. Thus, the fitting shaft 17 is fitted into the fitting hole 19, by means of a fixture, for mounting as well as fixing for retention of a predetermined positional relation. The fixture, by way of example, comprises a knob 22. The second attaching/detaching part 18 is provided with a threaded hole 21 which passes through the fitting hole 19 in a direction orthogonal thereto. The knob 22 has a male screw portion which can be threaded into the threaded hole 21. Therefore, by threading the knob 22 into the threaded hole 21, the fitting shaft 17 fitted into the fitting hole 19 can be fixed.

The first attaching/detaching part 15, the second attaching/detaching part 18 and the knob 22 constitute a principal part of a unit-to-unit connecting device (detachable connecting means).

It is to be understood that the structure of the unit-to-unit connecting device, without limitation to the one described above, may only be the one that can couple between the device housings of the imaging unit 1 and the display unit 2, respectively, in a predetermined direction. For example, the two units may be coupled by being fitted to each other first and then turned for locking, or may be coupled by fastening outer sides of connecting parts to each other by means of a fastener, or various other approaches may be employed.

As shown in FIG. 1, the display unit 2 is three-dimensionally movable by using a first retention frame 31 and can be unmovably supported at any position. Further, the imaging unit 1, as shown in FIG. 2, is three-dimensionally movable by using a second retention frame 32 and can be unmovably supported at any position.

The first retention frame 31 comprises a base 33 to be fixed to a surface of a floor F, a pillar 34 and a support arm 35. The support arm 35 is structured as an articulated arm having a first arm 36a and a second arm 36b. The first arm 36a is movably coupled to the pillar 34 through a first spherical bearing 37a. The first arm 36a and the second arm 36b are movably coupled to each other through a second spherical bearing 37b.

The display unit 2 is adapted to be detachably attached to an end of the second arm 36b of the support arm 35 via an attaching/detaching joint (unit-to-arm detachable device) 38. The attaching/detaching joint 38 may be attached to the end of the second arm 36b, or may be attached, for example, to a side face of the display unit 2, so that the display unit 2 can be detachably coupled to the end of the second arm 36b. It should be noted that the display unit 2 may be fixedly provided at the end of the second arm 36b.

The first spherical bearing 37a and the second spherical bearing 37b are arranged to have friction so that the support arm 35 would not move by itself with a moment generated by weight imposed at the end of the arm. Utilizing this friction, the support arm 35 (the first arm 36a and the second arm 36b) may be freely moved by hand, and moreover the support arm 35 is allowed to remain unmovable at a position to which it has been moved.

Alternative to the support structure using the friction, a locking means may be added to the movable part of the support 35 to enable selective operation. An arrangement may be made where the support arm 35 is allowed to be unmovable by utilizing the locking means. Alternatively, for example, an electromagnetic brake may be incorporated into each of the spherical bearings 37a and 37b, so that the arms can be movable/unmovable in response to an input through a switch.

The second retention frame 32 shown in FIG. 2 is structured substantially in the same manner as the first retention frame 31. Specifically, the second retention frame 32 comprises a base 12 to be fixed to a surface of a floor F, a pillar 42 and a support arm 43.

The support arm 43 is structured as an articulated arm having a first arm 46a and a second arm 46b. The first arm 46a is movably coupled to the pillar 42 through a first spherical bearing 47a. The first arm 46a and the second arm 46b are movably coupled to each other through a second spherical bearing 47b. The imaging unit 1 is adapted to be detachably attached to an end of the second arm 46b of the support arm 43 via an attaching/detaching joint (unit-to-arm detachable device) 48. The attaching/detaching joint 48 may be attached to the end of the second arm 46b, or may be attached, for example, to a side face of the imaging unit 1, so that the imaging unit 1 can be detachably coupled to the end of the second arm 46b.

The first spherical bearing 47a and the second spherical bearing 47b are arranged to have friction so that the support arm 43 would not move by itself with a moment generated by weight imposed at the end of the arm. As described above, a locking means may be added to the movable part of the support 43 to enable selective operation, thereby allowing the support arm 43 to be unmovable.

Next, the operation of the monitor microscope of the present embodiment is described below.

FIG. 1 shows a state of the imaging unit 1 and the display unit 2 in use being integrally coupled to each other (coupled state). This coupled state is attained by fitting the fitting shaft 17 of the display unit 2 into the fitting hole 19 of the imaging unit 1, and tightening the knob 22 for linkage of the fitting shaft 17 with the fitting hole 19, thereby bringing the imaging unit 1 and the display unit 2 into the coupled state. Since the imaging unit 1 has thus been mounted on the display unit 2, use of only the first retention frame 31 suffices operation, i.e. the second retention frame 32 does not have to be used.

As shown in FIG. 1, when the imaging unit 1 is directed toward the treatment site 4 of a subject, flux of light from the treatment site 4 taken by the objective lens 5 forms an image on a light receiving surface of the imaging element 8 through the imaging lens 6. This image is picked up by the imaging element 8. An image signal of thus obtained image of the treatment site 4 is input to the CCU 9 through the signal cable 10 for conversion into a video signal. The video signal is then transmitted to the display unit 2 through the video cable 11 to display the image on a monitor screen.

Firstly, effects of the imaging unit 1 and the display unit 2 in the coupled state, as shown in FIG. 1, are described.

In the coupled state, an operator may attempt to observe the treatment site 4 of a subject from different directions. On this occasion, the operator may move the imaging unit 1 left and right, or in a horizontal direction, or may tilt the imaging unit 1, utilizing a movable region of the spherical bearings 37a and 37b of the support arm 35 of the first retention frame 31. Meanwhile, the display unit 2, being integrally fixed to the imaging unit 1, naturally follows the movement of the imaging unit 1. Accordingly, the operator observing the display unit 2 naturally results in moving or tilting his/her body.

Next, a state of the imaging unit 1 and the display unit 2 in use being separated from each other (separated state) is described below.

When separating the imaging unit 1 and the display unit 2 from each other, the knob 22 is loosen to pull out the fitting shaft 17 from the fitting hole 19, thereby attaining the separated state. Then, as shown in FIG. 2, the imaging unit 1, being separated from the display unit 2 and independent, is attached to an end of the support arm 43 of the second retention frame 32.

In the separated state, an operator may attempt to observe the treatment site 4 of a subject from different directions. On this occasion, the operator may move the imaging unit 1 left and right, or in a horizontal direction, or may tilt the imaging unit 1, utilizing a movable region of the spherical bearings 47a and 47b of the support arm 43 of the second retention frame 32. Meanwhile, the display unit 2, being separated from the imaging unit 1, may be allowed to remain at its own location irrespective of the movement of the imaging unit 1. Accordingly, the operator observing the display unit 2 does not have to change his/her posture.

According to the present embodiment, selection may be made between the first state of use (coupled state shown in FIG. 1) where the position of the display unit 2 is allowed to change with the change of an observation direction of the imaging unit 1, and the second state of use (separated state shown in FIG. 2) where the display unit 2 is allowed to remain at its own location irrespective of the change of an observation direction of the imaging unit 1. Thus, in preparing for surgery, either of the uses can be selected depending on circumstances or preference of an operator.

In the second state of use described above, when an operator wishes to change the location of the display unit 2 alone, the operator may only have to move the support arm 35 of the first retention frame 31. Thus, the location of the display unit 2 can be changed independent of the imaging unit 1. On the other hand, when an operator wishes to change the location of the imaging unit 1 alone, the operator may only have to move the support arm 43 of the second retention frame 32. Thus, the location of only the imaging unit 1 can be changed independently.

As described heretofore, according to the present embodiment, the imaging unit 1 and the display unit 2 can be used by selecting either the coupled state or the separated state, depending on a preference of an operator. Alternatively, a surgery may be typically started with the imaging unit 1 and the display unit 2 being coupled, until a need arises for largely tilting the imaging unit 2 (i.e. need for observing a treatment site of a subject from quite an oblique direction), when the imaging unit 1 and the display unit 2 may be separated from each other. Accordingly, an operator can carry out a surgery, constantly being in an easy posture.

In the present embodiment, the fitting shaft 17 is used for performing attachment/detachment between the imaging unit 1 and the display unit 2. Needless to say, however, that other various attaching/detaching approaches may be employed, such as use of a magnetic material and use of fixing by means of a male screw and a female screw. Further, in the present embodiment, description has been given with a case of using spherical bearings having friction in order to movably retain the imaging unit 1 or the display unit 2, however, a so-called balanced pantograph arm may be alternatively used, in which a spring or a flange is used in combination with a parallelogram link. In this connection, taking into consideration of a case where weight imposed at the end of an arm is only of the display unit 2, and a case where weight of both of the imaging unit 1 and the display unit 2 is imposed, it is preferable to automatically adjust balance depending on the cases.

In the arrangement of the first embodiment as described above, the first state of use may be such that the imaging unit 1 may be attached to the end of the second retention frame 32, and that the display unit 2 may be attached to the imaging unit 1 by using the fitting means described above. Specifically, in this case, the second state of use may be such that the display unit 2 may be separated from the imaging unit 1 by releasing coupling means, and that the display unit 2 may be supported separately by the first retention frame 31, thereby ensuring the use shown in FIG. 2.

Second Embodiment

Figure 3:
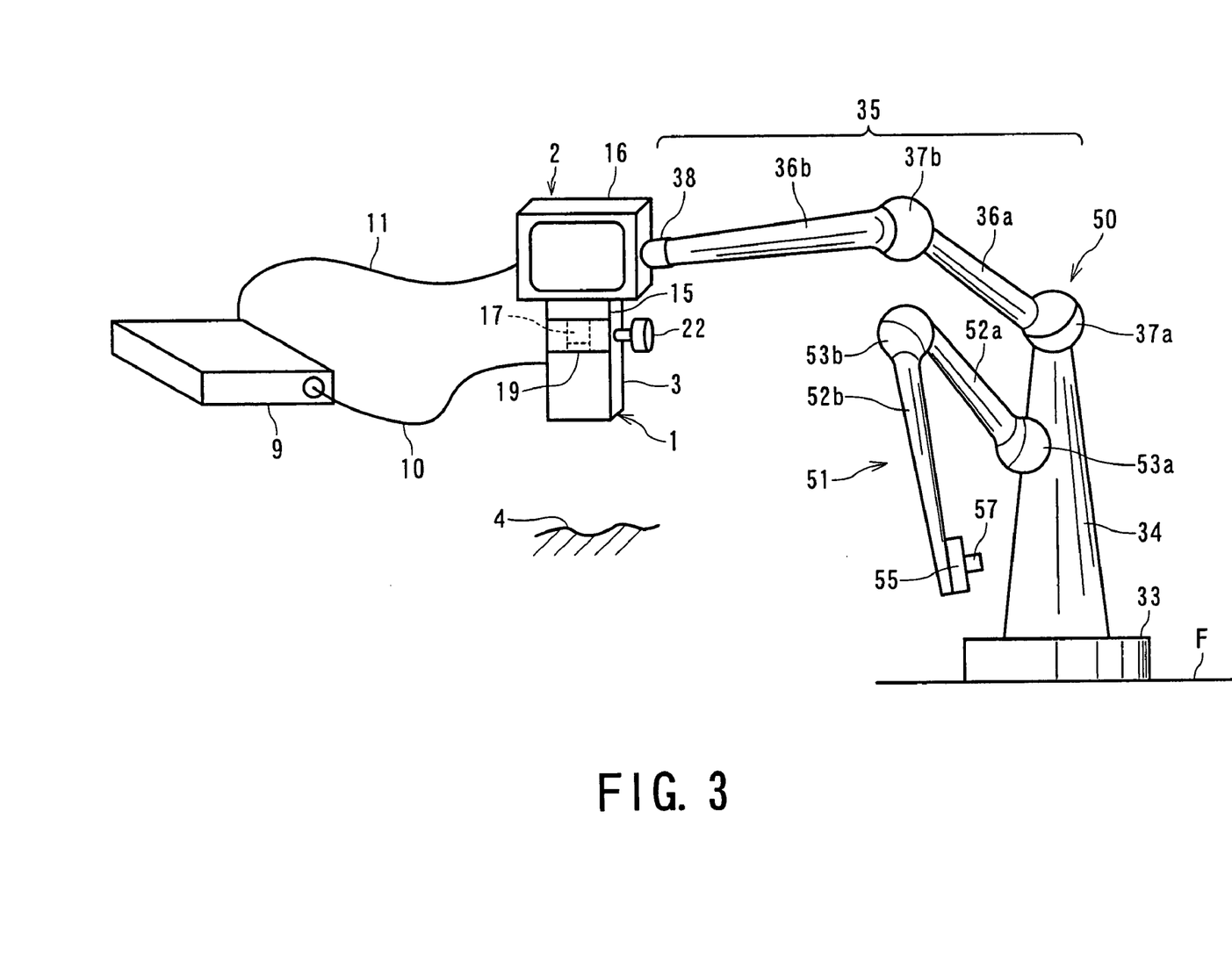
FIG. 3 is a schematic diagram of a monitor microscope in use, with an imaging unit and a display unit being coupled to each other, according to a second embodiment of the present invention.
Figure 4:
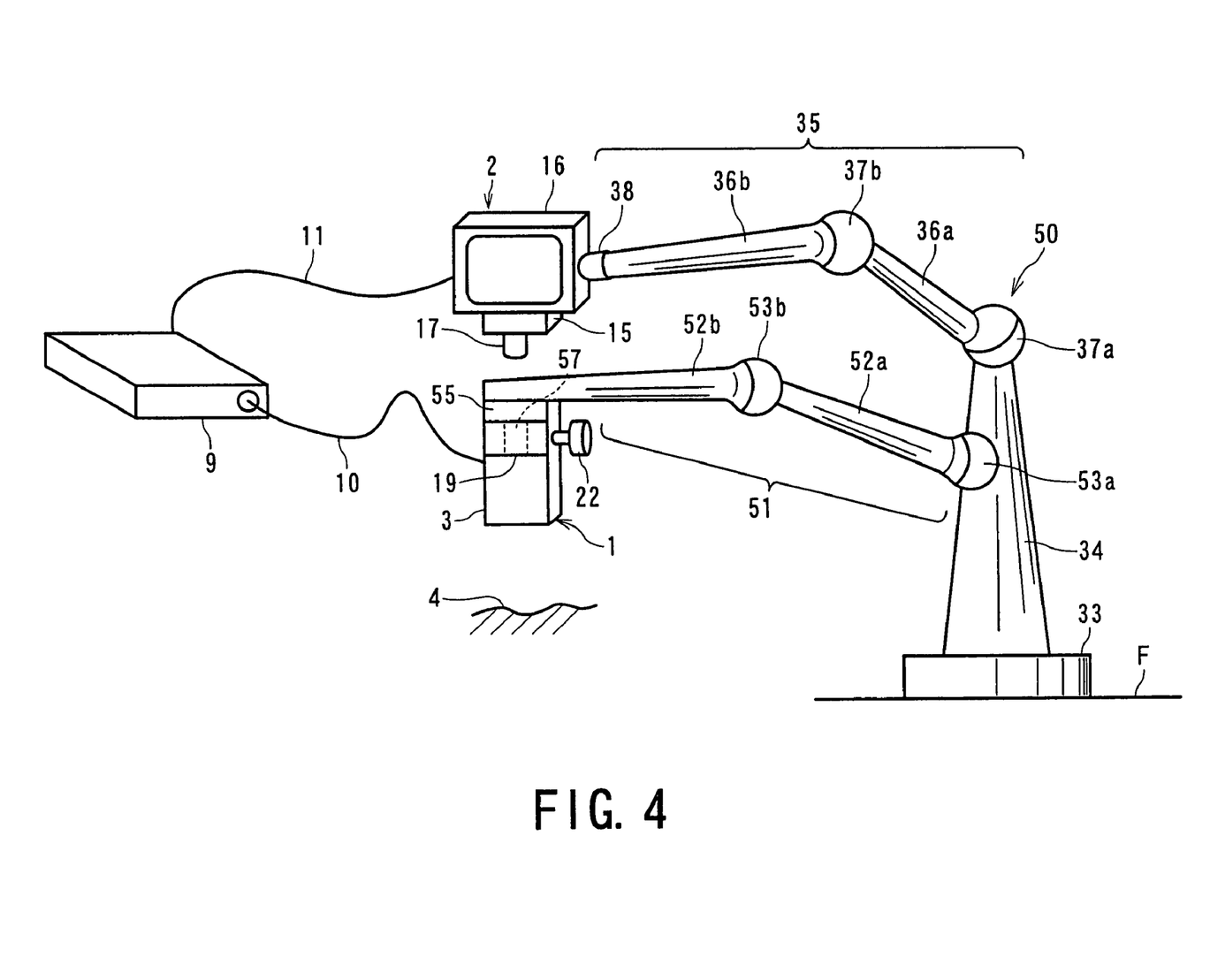
FIG. 4 is a schematic diagram of a monitor microscope in use, with an imaging unit and a display unit being separated from each other, according to the second embodiment of the present invention.

Referring now to FIGS. 3 and 4, a monitor microscope as an imaging and display system according to a second embodiment of the present invention is described hereinafter. Note that like components of an arrangement which is the same as the first embodiment, are referred to by like reference numerals to omit specific description therefor.

FIG. 3 shows a state of the imaging unit 1 and the display unit 2 in use, being coupled to each other (first state of use), and FIG. 4 shows a state of the imaging unit 1 and the display unit 2 in use, being separated from each other (second state of use).

In the present embodiment, the imaging unit 1 and the display unit 2 are configured approximately the same as those of the first embodiment described above, but the present embodiment is characteristic in that it is structured so that both of the imaging unit 1 and the display unit 2 may be supported by a single retention frame 50.

As shown in FIG. 3, the present embodiment provides the single retention frame 50 comprising the base 33, the pillar 34 and the support arm 35 as with the first retention frame 31 of the first embodiment described above.

The support arm 35 comprises the first arm 36a and the second arm 36b. The first arm 36a is movably coupled to the pillar 34 through the first spherical bearing 37a. The first arm 36a and the second arm 36b are movably coupled to each other through the second spherical bearing 37b. The display unit 2 is fixedly or detachably attached, via the attaching/detaching joint 38, to the end of the second arm 36b of the support arm 35.

In the present embodiment the retention frame 50 is provided, other than the arm 35 for supporting the display unit 2, with another arm 51 branching out from the pillar 34 so as to support the imaging unit 1. As shown in FIG. 4, the support arm 51 for the imaging unit 1 is structured as an articulated arm having a first arm 52a and a second arm 52b. The first arm 52a is movably coupled to the pillar 34 through a first spherical bearing 53a. The first arm 52a and the second arm 52b are movably coupled to each other through a second spherical bearing 53b. An electromagnetic brake (not shown) is incorporated into each of the first spherical bearing 53a and the second spherical bearing 53b, so that the arms can be movable/unmovable in response to an input from a switch.

The support arm 51 for the imaging unit 1 is provided, at the end of the second arm 52b thereof, with a third attaching/detaching part 55 for detachably mounting thereon the imaging unit 1. The third attaching/detaching part 55 is arranged similar to the first attaching/detaching part 15 described above. Specifically, as shown in FIG. 4, a fitting shaft 57 projecting downward and having a diameter A is formed at the third attaching/detaching part 55.

In the present embodiment, the first attaching/detaching part 15 and the third attaching/detaching part 55 constitute the unit-to-arm detachable device.

The effects of the present embodiment are described below.

As shown in FIG. 3, in a first state of use, where the imaging unit 1 and the display unit 2 are used being integrally coupled, the support arm 35 is allowed to support, at its end, the display unit 2, with the first unit 1 being integrally coupled to the display unit 2, as with the first embodiment. Meanwhile, the other arm 51 is folded and put way, as shown in FIG. 3.

In the second state of use, where the imaging unit 1 and the display unit 2 are used being separated from each other, the knob 22 mentioned above is released to pull out the fitting shaft 17 at the side of the display unit 2 from the fitting hole 19 at the side of the imaging unit 1 for separating the imaging unit 1 from the display unit 2. Then, as shown in FIG. 4, the arm 51 for the imaging unit 1 is extended to have the fitting shaft 57 at the third attaching/detaching part 55 inserted into the fitting hole 19 at the side of the imaging unit 1. Then the knob 22 is tightened to fix the imaging unit 1 to the arm 51.

As shown in FIG. 3, in the first state of use, where the imaging unit 1 and the display unit 2 are used being integrally coupled, an operator may attempt to observe the treatment site 4 of a subject from different directions. On this occasion, the operator may move the imaging unit 1 left and right, or in a horizontal direction, or may tilt the imaging unit 1. The display unit 2, being integrally fixed to the imaging unit 1, naturally moves with the imaging unit 1. Accordingly, the operator observing the display unit 2 has to cope with the movement of the units by moving or tilting his/her body.

As shown in FIG. 4, in the second state of use, where the imaging unit 1 and the display unit 2 are separated from each other, when an operator observes the treatment site 4 of a subject, the operator may attempt to observe the treatment site 4 of a subject from different directions. On this occasion, the operator may move the imaging unit 1 left and right, or in a horizontal direction, or may tilt the imaging unit 1, utilizing a movable region of the spherical bearings 53a and 53b of the support arm 51. Meanwhile, the display unit 2, being separated from the imaging unit 1, may be allowed to remain at its own location irrespective of the movement of the imaging unit 1. Accordingly, the operator observing the display unit 2 does not have to change his/her posture. Further, when an operator wishes to change the location of the display unit 2, the location of the display unit 2 alone can be changed independent of the imaging unit 1, by moving the arm 35 for the display unit 2.

According to the present embodiment, in addition to the effects obtained by the first embodiment described above, another advantage is provided that only a single retention frame will suffice. Therefore, manufacturing costs of the entire system can be reduced. Moreover, still another advantage is provided that a space occupied in an operation room can be reduced. This advantage may contribute to eliminating a problem that spaces for assistants and nurses to stand are difficult to be retained in an operation room because various pieces of medical equipment or anesthesia apparatuses are located in the operation room.

A modified example of the second embodiment described above may be provided, in which the display unit 2 is coupled to one arm 51, one of the two arms 35 and 51, to constantly fixedly support the imaging unit 1 (first state of use), and, when occasion demands, the display unit 2 is separated from the imaging unit 1 so as to be supported by another arm 35 (second state of use). In short, the modified example is the one in which an arm for supporting and an object to be supported are inverse of the arrangement shown in FIGS. 3 and 4.

Third Embodiment

Figure 5:
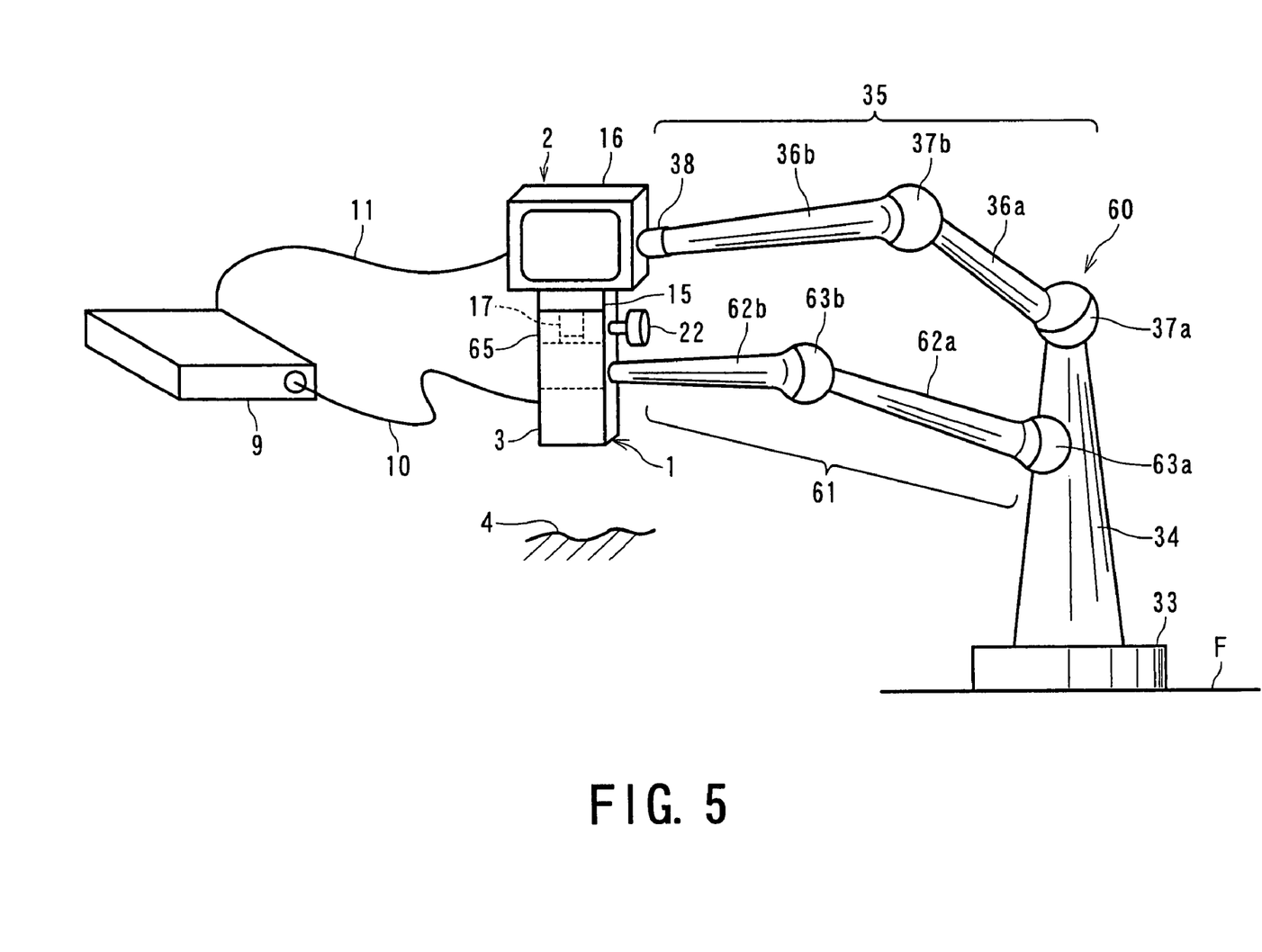
FIG. 5 is a schematic diagram of a monitor microscope in use, with an imaging unit and a display unit being coupled to each other, according to a third embodiment of the present invention.
Figure 6:
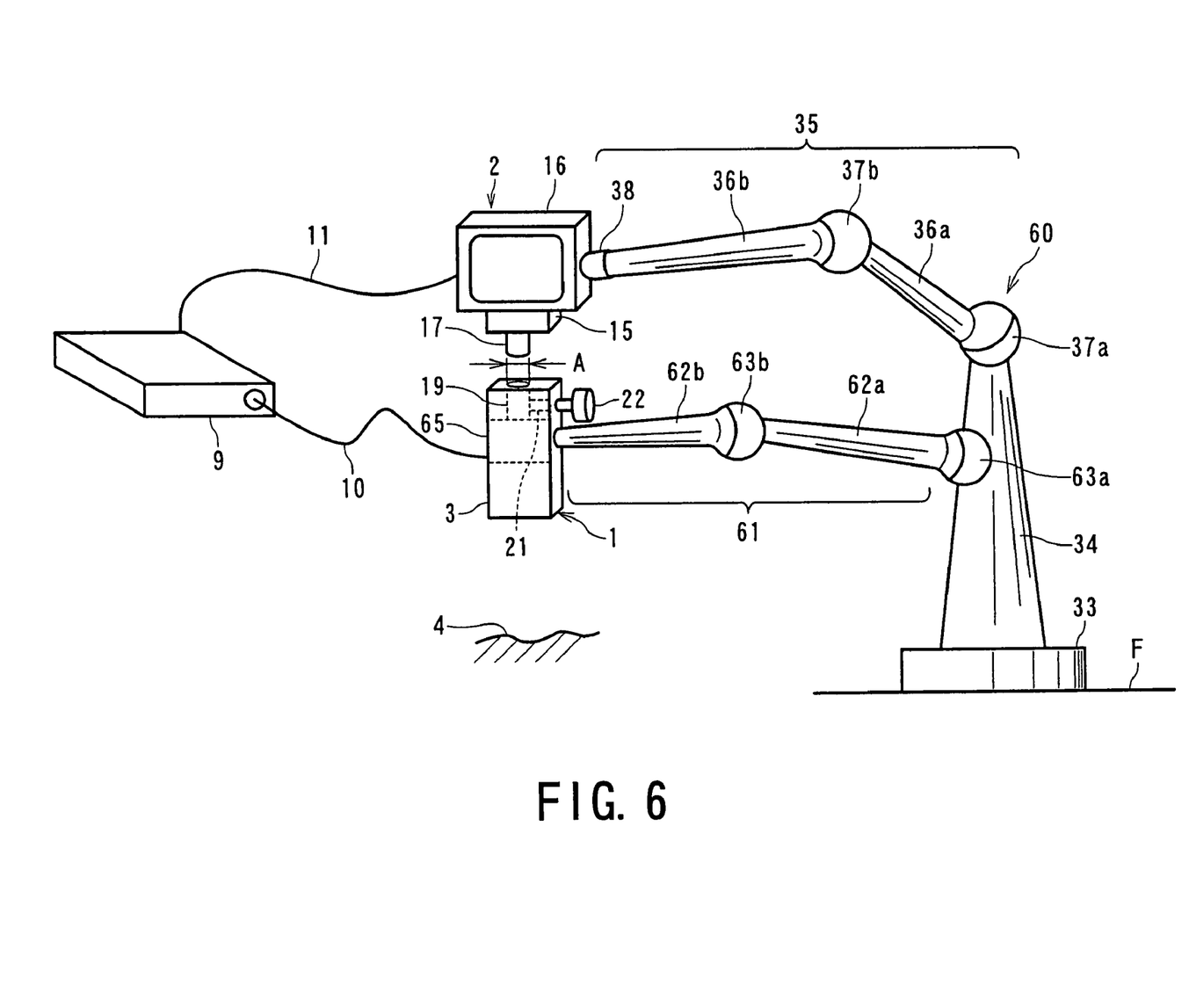
FIG. 6 is a schematic diagram of a monitor microscope in use, with an imaging unit and a display unit being separated from each other, according to the third embodiment of the present invention.

Referring to FIGS. 5 and 6, a monitor microscope as an imaging and display system according to a third embodiment of the present invention is described below. Note that like components of an arrangement which is the same as the first embodiment, are referred to by like reference numerals to omit specific description therefor.

FIG. 5 shows a state in which the imaging unit 1 and the display unit 2 are in use, being coupled to each other (first state of use), and FIG. 6 shows a state in which the imaging unit 1 and the display unit 2 are in use, being separated from each other (second state of use).

The imaging unit 1 and the display unit 2 of the present embodiment are characteristic, as with the ones in the second embodiment described above, in that both of the imaging unit 1 and the display unit 2 are constantly supported by a single retention frame, and that both of the units 1 and 2 can be separated from each other as occasion demands.

As shown in FIG. 5, the present embodiment comprises a single retention frame 60. As is the case with the first retention frame 31 shown in the first embodiment described above, the retention frame 60 comprises the base 33, the pillar 34 and the support arm 35. The support arm 35 has the same structure as the one in the second embodiment.

The retention frame 60 of the present embodiment is provided with a support arm 61 at its pillar 34 other than the support arm 35. The support arm 61 is configured such that it constantly supports the imaging unit 1. Specifically, in the present embodiment, two different support arms, i.e. the support arm 35 for the display unit 1 and the support arm 61 for the imaging unit 2 are both provided to the pillar 34 of the single retention frame 60.

As shown in FIGS. 5 and 6, the support arm 61 is structured as an articulated arm having a first arm 62a and a second arm 62b. The first arm 62a is movably coupled to the pillar 34 through a first spherical bearing 63a. The first arm 62a and the second arm 62b are movably coupled to each other through a second spherical bearing 63b. An electromagnetic brake (not shown) is incorporated into each of the first spherical bearing 63a and the second spherical bearing 63b, so that the arms can be movable/unmovable in response to an input from a switch.

The display unit 2 is fixedly or detachably attached to the end of the second aim 62b of the support arm 61. In the present embodiment, a mounting part 65 for detachably mounting the device housing 3 of the imaging unit 1 and the second arm 62b are integrally formed in a fixed state.

As shown in FIG. 6, the fitting hole 19 having a diameter A to fit with the fitting shaft 17 of the display unit 2, is formed at an upper end portion of the mounting part 65. It is configured such that the fitting shaft 17 is fitted into the fitting hole 19 while tightening the above described knob 22 so that the display unit 2 is coupled to be fixed, retaining a predetermined positional relation.

The effects of the present embodiment are described below.

As shown in FIG. 5, in the first state of use where the imaging unit 1 and the display unit 2 are used being integrally combined, as with the first embodiment described above, the display unit 2 is supported at the end of the support arm 35, and the imaging unit 1 is integrally assembled into the display unit 2. Further, the imaging unit 1 is supported at the end of another support arm 61.

In the first state of use, when an operator observes the treatment site 4 of a subject, the operator may attempt to observe the treatment site 4 from different directions. On this occasion, the operator may move the imaging unit 1 left and right, or in a horizontal direction, or may tilt the imaging unit 1. As the display unit 2 is integrally fixed to the imaging unit 1, the display unit 2 naturally moves with the imaging unit 1. Thus, the operator, who observes the treatment site 4 through the display unit 2, copes with the movements of the units by moving or tilting him/herself.

In the second state of use, as shown in FIG. 6, where the imaging unit 1 and the display unit 2 are used being separated from each other, the knob 22 is released to pull out the fitting shaft 17 at the side of the display unit 2 from the fitting hole 19 at the side of the imaging unit 1, so that the imaging unit 1 is separated from the display unit 2. As shown in FIG. 6, the imaging unit 1 is allowed to be solely supported by the support arm 61, and the display unit 2 is allowed to be solely supported by the support arm 35. Thus, the imaging unit 1 and the display unit 2 establish the second state of use where they can be independently moved.

In the second state of use, as shown in FIG. 6, when an operator attempts to observe the treatment site 4 of a subject, the operator may move the imaging unit 1 left and right. Further, when the operator attempts to observe the treatment site 4 from a direction different from a current direction of observation, the operator may move the imaging unit 1 in a horizontal direction, or may tilt the imaging unit 1, utilizing the movable ranges of the spherical bearings 63a and 63b of the arm 61. However, the display unit 2, which is separated from the imaging unit 1, can remain at its own location irrespective of the movement of the imaging unit 1. Accordingly, an operator, who observes the treatment site 4 through the display unit 2, does not have to change his/her posture. When an operator wishes to change the location of the display unit 2, the operator can move the support arm 35 for the display unit 2, so that the imaging unit 1 and the display unit 2 can independently change their locations.

According to the present embodiment, the imaging unit 1 and the display unit 2 may be readily separated from each other by only releasing the knob 22 to pull out the fitting shaft 17, while dispensing with attachment/detachment labor with respect to the support arm 61. In short, transit from the first state of use to the second state of use may be readily done. Needless to say that transit from the second state of use to the first state of use may be readily done. Thus, in addition to the advantages obtained from the first embodiment, the present embodiment provides another advantage of facilitating transit from the first state of use to the second state of use, or vice versa, during a surgery. In particular, comparing with the second embodiment, omission of labor for attaching/detaching the imaging unit 1 to/from the support arm 61 may provide further advantage.

(Modification)

Figure 7:
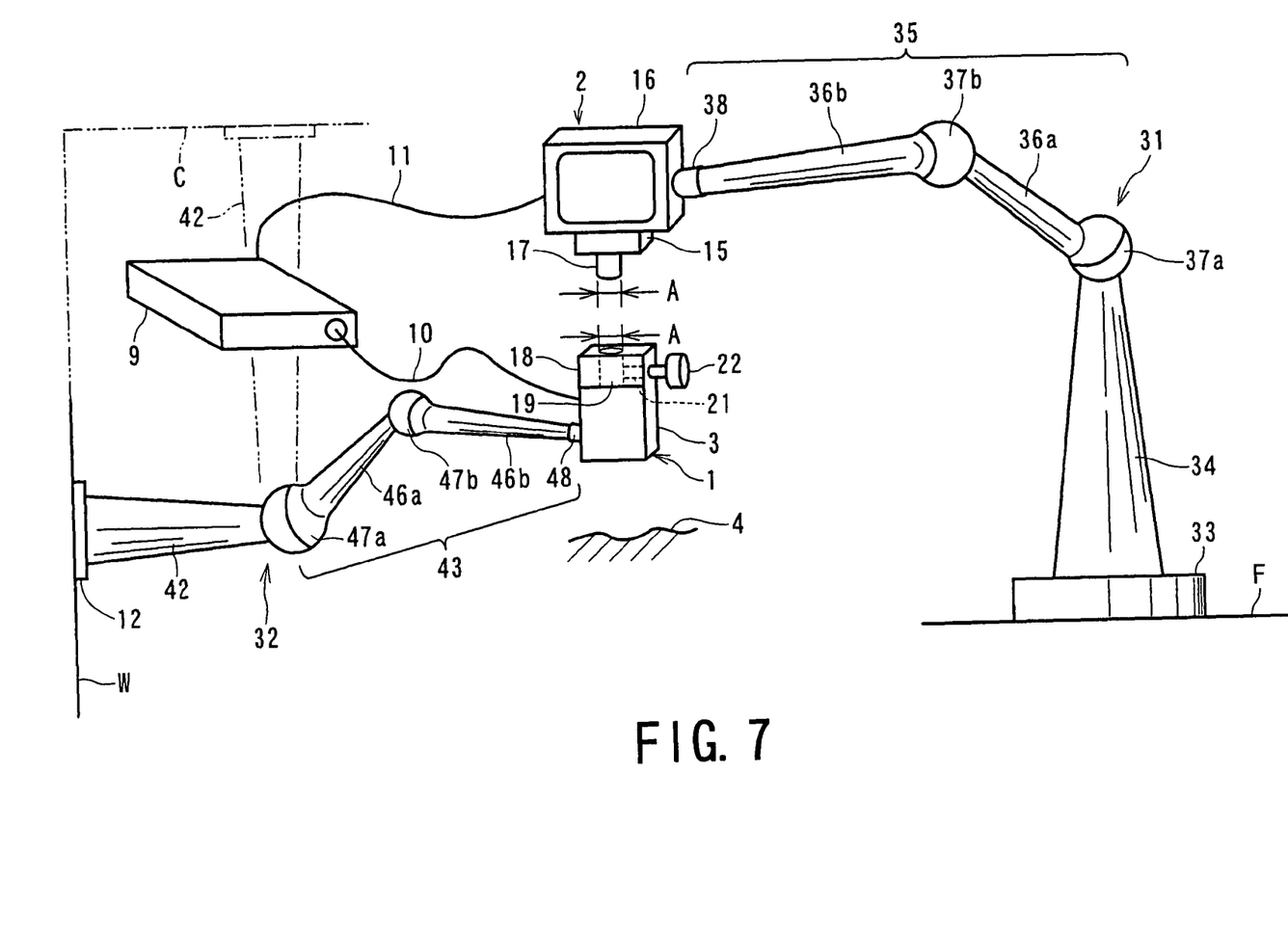
FIG. 7 is a schematic diagram showing a monitor microscope according to a modified example of the present invention.

FIG. 7 shows an example of a modulation in fixing positions of arms for supporting the imaging unit 1 and the display unit 2. The monitor microscope as an imaging and display system shown in FIG. 7, is in the second state of use as described hereinbefore and shown in FIG. 2. As can be seen from FIG. 7, two arms 35 and 43 for supporting pillars 34 and 42, respectively, are provided, with one, of the pillars, the pillar 42, being provided on a wall surface W (portion to be fixed), thereby saving space. Further modulation may be made as can be seen at an imaginary line in FIG. 7 where the pillar 42 is fixed to a ceiling C (portion to be fixed) of a building.

It should be noted that an arrangement wherein surfaces of floor, wall or ceiling are utilized as portions to be fixed as mentioned above, may be applicable to the support of the other arm 35, as well as to all the arms described in the second and the third embodiments.

The embodiments of the present invention have been described heretofore. However, the present invention is not limited to the embodiments and modulation described herein but may be applicable to other embodiments. Accordingly, various modulations of the present invention, without limitation to the embodiments or modulation described herein, can be implemented in other embodiments without departing from the spirit and the scope of the invention. For example, the imaging and display system of the present invention is not necessarily limited to the use for a surgical imaging microscopic device, but may be applicable to other monitoring systems, such as a system for monitoring manufacturing lines, in which an imaging unit and a display unit are integrally or separately used.

What is claimed is:

1. An imaging and displaying system comprising:
an imaging unit that images a region to be targeted of a subject to be examined;
an image producing unit that produces an image based on data imaged by the imaging unit.
a display unit that displays the image produced by the image producing unit;

a support member that spatially, movably, and mechanically supports at least one of the imaging unit and the display unit; and a unit-to-unit connecting device that detachably, mechanically, and directly connects the imaging unit and the display unit with each other such that the support member spatially movably supports the imaging unit and the display unit in a state where the imaging unit and the display units are mechanically unified with each other.

2. The system according to claim 1, wherein the support member comprises a first arm spatially movably supporting the imaging unit, and a second arm spatially movably supporting the display unit.

3. The system according to claim 2, comprising a unit-to-arm detachable device arranged between the at least one of the imaging and displaying units and the first and second arms, wherein at least one of the imaging unit and the display unit is detachably secured to an arm selected from the first and second arms by using the unit-to-arm detachable device intervening therebetween.

4. The system according to claim 3, wherein the unit-to-arm detachable device intervenes between the imaging unit and the first arm.

5. The system according to claim 3, wherein the unit-to-arm detachable device intervenes between the imaging unit and the second arm.

6. The system according to claim 2, wherein the first and second arms are built to extend from a single common pillar member.

7. The system according to claim 6, wherein at least one of the imaging unit and the display unit is detachably secured to an arm selected from the first and second arms by using a unit-to-arm detachable device intervening therebetween.

8. The system according to claim 7, wherein the unit-to-arm detachable device intervenes between the imaging unit and the first arm.

9. The system according to claim 7, wherein the unit-to-arm detachable device intervenes between the imaging unit and the second arm.

10. The system according to claim 2, wherein the first and second arms are built to extend from different pillar members, respectively.

11. The system according to claim 10, wherein at least one of the imaging unit and the display unit is detachably secured to an arm selected from the first and second arms by using a unit-to-arm detachable device intervening therebetween.

12. The system according to claim 11, wherein the unit-to-arm detachable device intervenes between the imaging unit and the first arm.

13. The system according to claim 11, wherein the unit-to-arm detachable device intervenes between the imaging unit and the second arm.

14. The system according to claim 2, wherein one of the first and second arms is built to extend from a pillar member and the other is built to extend from a fixed portion of a building, the fixed portion including at least one of a floor, a wall, and a ceiling of the building.

15. The system according to claim 14, wherein at least one of the imaging unit and the display unit is detachably secured to an arm selected from the first and second arms by using a unit-to-arm detachable device intervening therebetween.

16. The system according to claim 15, wherein the unit-to-arm detachable device intervenes between the imaging unit and the first arm.

17. The system according to claim 11, wherein the unit-to-arm detachable device intervenes between the imaging unit and the second arm.

18. The system according to claim 9, wherein both of the unit-to-arm detachable device and the unit-to-unit connecting device are formed to have a common shape permitting attachment/detachment operations to/from the imaging unit.

19. The system according to claim 2, wherein the first and second arms are polyarticular arms, respectively.

20. The system according to claim 1, wherein the imaging unit is an imaging unit acquiring reflected light from the region to be targeted of the subject as image information processed into digital electric signals and both the imaging unit and the display unit compose a monitor microscope handling digital images.

21. An imaging and displaying system comprising:

an imaging unit configured for imaging a region to be targeted of a subject to be examined, the imaging unit having a housing;

an image producing unit that produces an image based on data imaged by the imaging unit;

a display unit configured for displaying the image produced by the image producing unit, the display unit having a housing;

a unit-to-unit connecting device detachably, mechanically, and directly configured to connect the imaging unit and the display unit with each other;

a first arm spatially movably configured for supporting the imaging unit;

a second arm spatially movably configured for supporting the display unit; and at least one pillar member configured for supporting the first and second arms, wherein the unit-to-unit connecting device comprises a first attaching/detaching part secured on the housing of the imaging unit, a second attaching/detaching part secured on the housing of the display unit, and a securing member configured to securely couple the first attaching/detaching part and the second attaching/detaching part with each other.

22. The system according to claim 21, comprising a unit-to-arm detachable device configured for detachably securing at least one of the imaging unit and the display unit to an arm designated from the first and second arms by using a unit-to-arm detachable device.

23. The system according to claim 21, wherein the at least one pillar member is a single common pillar member configured for supporting the first and second arms.

24. The system according to claim 21, wherein the at least one pillar member are two pillar members configured for supporting the first and second arms, respectively.

25. The system according to claim 21, wherein the at least one pillar member is two in number, one of the first and second arms is built to one of the pillar members, and the other of the first and second arms is built to another arm secured to a fixed portion of a building, the fixed portion including at least one of a floor, a wall, and a ceiling of the building.

26. The system according to claim 21, wherein the first and second arms are polyarticular arms, respectively.

27. The system according to claim 21, wherein the securing member is configured to securely couple the first attaching/detaching part and the second attaching/detaching part with each other such that the housing of the imaging unit and the housing of the display unit are directly attached to each other.

* * * * *